(12) United States Patent
Tanaka et al.

(10) Patent No.: US 6,309,674 B1
(45) Date of Patent: Oct. 30, 2001

(54) THERAPEUTIC AGENTS FOR RESPIRATORY DISEASES

(75) Inventors: Masaya Tanaka, Kobe; Masato Hiki, Osaka, both of (JP)

(73) Assignee: Medion Research Laboratories, Hyogo (JP)

( * ) Notice: Subject to any disclaimer, the term of this patent is extended or adjusted under 35 U.S.C. 154(b) by 0 days.

(21) Appl. No.: 09/424,265

(22) PCT Filed: May 21, 1998

(86) PCT No.: PCT/JP98/02237

§ 371 Date: Nov. 19, 1999

§ 102(e) Date: Nov. 19, 1999

(87) PCT Pub. No.: WO98/52588

PCT Pub. Date: Nov. 26, 1998

(30) Foreign Application Priority Data

May 21, 1997 (JP) .................................... 9/131059

(51) Int. Cl.[7] .......................... A61K 35/78; A61K 39/385
(52) U.S. Cl. ......................... 424/725; 424/769; 424/773; 424/774; 424/775; 424/776; 424/777; 424/779; 514/26; 514/169; 514/826; 514/863; 514/885; 514/887
(58) Field of Search .............................. 514/26, 169, 826, 514/863, 885, 887; 424/725, 769, 773, 774, 775, 776, 777, 779

(56) References Cited

U.S. PATENT DOCUMENTS

| | | | |
|---|---|---|---|
| 4,323,468 | 4/1982 | Grollier et al. ................. 252/174.17 |
| 4,604,282 | * 8/1986 | Grollier et al. ........................ 424/74 |
| 4,604,284 | 8/1986 | Kung et al. .............................. 424/85 |
| 4,703,053 | * 10/1987 | Connor et al. ....................... 514/382 |
| 5,683,698 | * 11/1997 | Chavali et al. .................... 424/195.1 |
| 5,703,098 | * 12/1997 | Muller et al. ......................... 514/339 |

FOREIGN PATENT DOCUMENTS

| | | |
|---|---|---|
| 54-3930 | 2/1979 | (JP) . |
| 55-157508 | 12/1980 | (JP) . |
| 7-196526 | 8/1995 | (JP) . |
| 8-53360 | * 2/1996 | (JP) .................................. 424/195.1 |

OTHER PUBLICATIONS

Derwent Abstract 1997–320252, "Oral Liquid for Treating Rheumatoid Disease and Cancer", Jul. 1995.*
Derwent Abstract 1995–241307, "Traditional Chinese Medicine for Treating Psoriasis", Jul. 1994.*
The Merck Manual, Section 10, Chapter 117, Scaling Papular Diseases (2000). (www.merck.com/pubs/mmanual/section10/chapter 117/117b.htm).
"Fucyclopedia of Naturally Occurring Drugs (in Japanese)", K.K. Hirokawa Shoten, Apr. 15, 1986, 16th print, p. 175, description concerning Smilax China.
Kaneyoshi Akamatsu, "Chinese and Japanese Medicines: Newly Revised Edition (in Japanes)", Ishiyaku Shuppan K.K., Oct. 15, 1980, 1st edition, 5th print, pp. 565–566.
International Search Report (3/99).
Partial English Translation of "Fucyclopedia of Naturally Occurring Drugs (in Japanese)", p. 175, (1986) and partial thereof.
Partial English Translation of "Chinese and Japanese Medicines: Newly Revised Edition (in Japanese)", p. 565, (1980).

* cited by examiner

*Primary Examiner*—Frederick Krass
(74) *Attorney, Agent, or Firm*—Sughrue, Mion, Zinn, Macpeak & Seas, PLLC

(57) ABSTRACT

Prophylactic or therapeutic agents for respiratory diseases, allergic diseases, keratosis, and carcinomatous pain, containing Smilax china or a plant analogous thereto as the active ingredient. These agents can improve the condition and predisposition of acute and chronic respiratory diseases, such as acute bronchitis, bronchial asthma, asthmatic bronchitis, chronic bronchitis, pan bronchiolitis and bronchiectasis, allergic diseases, such as atopic dermatitis, pollinosis, allergic rhinitis and allergic conjunctivitis, and keratosis, such as psoriasis, lichen, ichthyosis, furfur, and palmoplantar keratosis without side effects and at the same time can lower serum IgE level on an abnormally high level in a short period of time. After the symptom and predisposition have been improved, these agents can, even after suspension of administration, persistently lower the serum IgE level and in addition can inhibit the recurrence of the symptom.

7 Claims, No Drawings

THERAPEUTIC AGENTS FOR RESPIRATORY DISEASES

This application is a 371 of PCT/JP98/02237, filed May 21, 1998.

1. Technical Field

The therapeutic agent for respiratory disease according to this invention relates to a prophylactic or therapeutic drug for respiratory diseases, a prophylactic or therapeutic drug for allergic diseases, a prophylactic or therapeutic drug for keratosis, a prophylactic or therapeutic drug for carcinomatous pain, a health food, a performance food, a cosmetic additive and a cosmetic product, which are capable of improving the symptom of, and the predisposition to, acute and chronic respiratory diseases, such as acute bronchitis, bronchial asthma, asthmatic bronchitis, chronic bronchitis, pan bronchiolitis and bronchiectasis, allergic diseases, such as atopic dermatitis, pollinosis, allergic rhinitis and allergic conjunctivitis, and keratosis, such as psoriasis, lichen, ichthyosis, furfur, and palmoplantar keratosis without side effects and at the same time capable of lowering serum IgE level on an abnormally high level in a short period of time. After the symptom and predisposition have been improved, these agents can, even after suspension of administration, persistently lower the serum IgE level if it is still abnormally high and in addition can inhibit the recurrence of the symptom.

2. Background Art

Acute and chronic respiratory diseases such as acute bronchitis, bronchial asthma, asthmatic bronchitis, chronic bronchitis, diffuse ordinary bronchiolitis and bronchiectasis are intractable diseases. The therapy of these diseases is generally a symptomatic treatment centered around temporary control of coughing with an antitussive or, in case respiratory distress intervenes, assisted respiration with a bronchodilator, although the treatment is not rewarding in cases of severe coughing. Moreover, bronchial asthma can be regarded as allergy and anti-allergics are also used for its prevention or therapy but the efficacy of such medication is not always reliable but even in patients with remission of the symptom, suspension of the administration results in recurrence of the symptoms. Adrenocortical hormones are administered in severe cases but, despite a certain rewarding effect they provide, sometimes cause intense side effects. Moreover, those, too, are symptomatic remedies. Thus, no drug is known of which recurrence of the symptom does not occur after suspension of administration. Health foods, for instance, are also available with claims to the effect that their intake leads to improvements in the patient's predisposition and a cure of diseases or control of symptoms but their efficacy is either not steadfast or has not been medically proven.

Keratosis is a representative chronic disease in dermatology, and the patients have genetic predisposition as a backgrounding factor in many cases but the cause remains to be identified. The therapy includes a topical therapy using an urea or steroid ointment and a systemic therapy using a retinoid (vitamin A derivative). In psoriasis, phototherapy is also performed. However, the therapeutic modalities so far used for keratosis are of limited effect and further have many drawbacks, for example they are symptomatic treatments or cause strong side effects.

Therefore, there has been a long-standing demand for a prophylactic or therapeutic drug for respiratory diseases, a prophylactic or therapeutic drug for allergic diseases and a prophylactic or therapeutic drug for keratosis, which, once improvements have been obtained in the symptom or predisposition, would be free from the recurrence problem following the suspension of administration.

Carcinomatous pain is an intractable symptom, in which narcotic analgesics are commonly used, but there are many problems; with those drugs, pain can hardly be fully controlled, side effects are very severe, and repeated administration leads to an attenuation of the effect. Non-narcotic analgesics are not as problematic but are used less often because their efficacy is weak. Under the circumstances, there has been a keen demand for a prophylactic or therapeutic drug for carcinomatous pain which would be potent enough with moderate side effects and free from attenuation of efficacy in repeated administration.

Meanwhile, Smilax china Linne is a naturally growing woodbine which has heretofore been used as a folk medicine in gonorrhea, syphilis, lumbago, neuralgia, rheumatism, nocturia, uremia and common cold but its efficacy as a prophylactic or therapeutic drug for respiratory diseases, such as bronchial asthma, allergic diseases, keratosis or carcinomatous pain has not been known.

DISCLOSURE OF INVENTION

As a result of their intensive investigation, the inventors of this invention found that Smilax china Linne or a plant analogous thereto is capable of improving the symptom, and the predisposition to, acute and chronic respiratory diseases, such as acute bronchitis, bronchial asthma, asthmatic bronchitis, chronic bronchitis, pan bronchiolitis and bronchiectasis, allergic diseases, such as atopic dermatitis, pollinosis, allergic rhinitis, allergic conjunctivitis, etc. and keratosis, such as psoriasis, lichen, ichthyosis, furfur, and palmoplantar keratosis without side effects and at the same time can lower serum IgE level on an abnormally high level in a short period of time. In addition, after the symptom and predisposition have been improved, these agents can, even after suspension of administration, persistently lower the serum IgE level and in addition can inhibit the recurrence of the symptom. The plant was also found to give an immediate relief of calcinomatous pain without side effects and without attenuation of the efficacy in repeated administration. The instant invention has been developed on the basis of the above findings.

This invention, therefore, is directed to a prophylactic or therapeutic drug for respiratory diseases, a prophylactic or therapeutic drug for allergic diseases, a prophylactic or therapeutic drug for keratosis and a prophylactic or therapeutic drug for carcinomatous pain, all containing Smilax china Linne as the active ingredient.

Smilax china Linne provides the above-mentioned effects even when ingested in the form of a health or a performance food, such as foods and drinks, or used in the form of a cosmetic additive or a cosmetic preparation.

(1) Active Ingredient

Smilax china Linne, which is used in this invention, is a naturally growing woodbine and its root, leaf, stem and fruit can be utilized. Those can be dried and directly ingested in various forms, such as finely minced, moderately minced, coarsely minced, finely pulverized, moderately pulverized, coarsely pulverized and finely pulverized forms, or in the form of an extract obtained by extraction with water, an organic solvent, such as alcohol (methanol, ethanol, propanol, butanol, etc.), acetone, ethyl acetate, chloroform, dichloromethane, dioxane or ether, or a hydrous organic solvent. The extraction solvent and extraction method can be freely selected and established. The extract obtained can be used as it is, after concentration (when water, ethanol, ethanol-water or the like has been used for extraction), or dried beforehand.

The plant analogous to Smilax china Linne means a plant which contains an active principle as that of Smilax china Linne, i.e. the principle showing efficacy in respiratory diseases, allergic diseases, keratosis or carcinomatous pain, thus including Smilax rhizoma, for instance.

(2) Prophylactic or therapeutic drugs for respiratory diseases, allergic diseases, keratosis and carcinomatous pain The active principle can be administered without particular limitation in ordinary oral dosage forms such as extracts, solutions, syrups, tablets, capsules, granules, fine granules, powders, pills, suspensions, hard plasters, ointments, lotions, infusions, and decoctions. Furthermore, it can be administered transmucosally as suppositories, inhalants or nasal drops. Moreover, one may ingest it in the form of a solution prepared by adding hot water to dried Smilax china Linne as if one would have a cup of tea. Those dosage forms may contain, in addition to the active ingredient or principle, the excipient, diluent, carrier and/or other additives which are commonly used in the pharmaceutical field.

The effective prophylactic or therapeutic amount of Smilax china Linne or a plant analogous thereto is dependent on the patient's clinical condition, age and body weight, among other factors, but the daily dose, as Smilax china Linne, per adult human, is 0.1 g~100 g, preferably 1 g~70 g, more preferably 3 g~30 g, and either the plant Smilax china Linne or an extract thereof is administered either in a single dose or in two or more divided doses a day. The desired effect is obtained at a daily dose of more than 100 g but such a dose escalation will not be rewarded with a significant increase in efficacy.

The respiratory disease which can be prevented or cured with the drug of this invention includes acute and chronic respiratory diseases, such as acute bronchitis, bronchial asthma, asthmatic bronchitis, chronic bronchitis, pan bronchiolitis, bronchiectasis, etc., preferably bronchial asthma, asthmatic bronchitis and chronic bronchitis, more preferably bronchial asthma and asthmatic bronchitis.

The allergic disease which can be prevented or cured with the drug of this invention includes atopic dermatitis, pollinosis, allergic rhinitis, allergic conjunctivitis, etc., preferably atopic dermatitis, allergic rhinitis and pollinosis, more preferably atopic dermatitis and pollinosis.

The keratosis which can be prevented or cured with the drug of this invention includes psoriasis, lichen, ichthyosis, furfur and palmoplantar keratosis, more preferably psoriasis or palmoplantar keratosis, much more preferably psoriasis vulgaris, pustular psoriasis, erythroderma psoriaticum and palmoplantar keratosis.

The carcinomatous pain which can be prevented or cured with the drug of this invention includes the carcinomatous pain associated with lung cancer, stomach cancer, renal cancer, liver cancer, rectal cancer, colon cancer, gallbladder cancer, cancer of the pancreas, ovary cancer, carcinoma of the uterine cervix, carcinoma of the body of uterus, testicular cancer, breast cancer, skin cancer, sarcoma of bone, etc., preferably the cacinomatous pain in lung cancer, stomach cancer, renal cancer, liver cancer, gallbladder cancer, cancer of the pancreas and sarcoma of bone, more preferably the carcinomatous pain associated with lung cancer, stomach cancer or liver cancer.

(3) Health Food and Performance Food

The health food and performance food according to this invention may be solid or semisolid foods or liquids (drinks). The health food or performance food is formulated with said active principle or ingredient. The formulating amount of the active principle in such a health food or performance food is usually equivalent to a daily intake of about 0.1 g~100 g, as Smilax china Linne, for an adult human but should more than 100 g be ingested, there is no risk for side effects.

Specifically, the health food and performance food include solid or semisolid foods such as bread, cookies, biscuits, rice-crackers, candies, gummy candies, jellies, puddings, ice cream, chocolates, etc. and drinks such as coffee, black tea, Japanese tea, oulong tea, fruit juices, cola drinks and carbonated drinks, among others.

(4) The Cosmetic Additives and Cosmetic Products

The above active ingredient is efficacious in allergic disease, such as atopic dermatitis, and keratosis, such as psoriasis, lichen, ichthyosis, furfur and palmoplantar keratosis and, as such, is effective as a cosmetic ingredient for cosmetic products including medicated cosmetics or in the form of cosmetic products containing said ingredient. The active ingredient is preferably formulated in the form of an extract.

The cosmetic products include lotions, creams, toilet waters, milk lotions, packs, soaps, oils, mousse and sprays, and such cosmetic products can be manufactured with the additives, which are conventionally included in cosmetic formulations, in addition to the active ingredient of the invention.

The prophylactic or therapeutic agent for respiratory disease according to this invention not only improves the symptom of, and the predisposition to, respiratory diseases, allergic diseases and keratosis but also lowers serum IgE level on an abnormally high level in a short period of time and, even if its administration is suspended after the symptom and predisposition have been improved, continues to lower the serum IgE level to inhibit the recurrence of the symptom.

Furthermore, any drug comprising Smilax china Linne or a plant analogous thereto as the active ingredient is useful as a therapeutic agent for carcinomatous pain with a persistent inhibitory effect on its recurrence even after suspension of administration and can be expected to express analgesic efficacy in cases of pain associated with, for example, a herpes simplex virus infection. In addition, its efficacy in the treatment of chronic renal insufficiency and viral hepatitis inclusive of chronic type B hepatitis and chronic type C hepatitis.

The following production examples, test examples and formulation examples are further illustrative of this invention.

BEST MODE FOR CARRYING OUT THE INVENTION

PRODUCTION EXAMPLE 1

The root and stem of Smilax china Linne were finely shorn with a pair of gardener's scissors and 15 g of the shearings were put in a 1-liter kettle containing 400 ml of water and boiled under a moderate fire until the quantity of water had been reduced to ½ to give 200 ml of a dark tan-colored liquor. This liquor was filtered and transferred to a 500 ml glass bottle. To the remaining Smilax china Linne was added 200 ml of water, and the mixture was boiled on a moderate fire until the quantity of water had been reduced to ½ to give 100 ml of a black tea-colored liquor. This liquor was filtered and the filtrate was added to the above liquor to provide 300 ml of a hot water extract of Smilax china Linne.

PRODUCTION EXAMPLE 2

The root and stem of Smilax china Linne were finely shorn with a pair of gardener's scissors and 2 g of the shearings were put in a tea bag (trademark: O-cha Pack, Marusan Sangyo K.K.). The filled bag was placed in a 200 ml tea cup and 160 ml of boiling water was poured over the bag, followed by gentle stirring with a spoon for 3 minutes, to provide 160 ml of a hot water extract of Smilax china Linne which was deep tan in color.

PRODUCTION EXAMPLE 3

The root and stem of Smilax china Linne were finely shorn with a pair of gardener's scissors and 50 g of shearings were put in a 1-liter kettle containing 500 ml of ethanol (Wako Pure Chemical Industries). The mixture was boiled on a moderate fire until the amount of ethanol had been reduced to 50 ml to provide an alcohol extract of Smilax china Linne which was deep tan in color.

PRODUCTION EXAMPLE 4

The root and stem of Smilax china Linne were finely pulverized with a pulverizer and 22 kg of the pulverizate was put in 440 liters of water and boiled for 2 hours to provide a deep tan-colored liquor. This liquor was filtered and further heated to provide 2.4 kg of a hot water extract of Smilax china Linne which was viscous and deep tan in color.

Formulation Example 1
(Cookies)

Salt-free butter, 100 g, was kneaded to a creamy consistency and stirred well with 60 g of sugar added. This mixture was further mixed with one beaten egg and 30 g of the pulverized root and stem of Smilax china Linne, followed by stirring. Then, 200 g of wheat flour and ½ teaspoonful of baking powder were added and the whole was kneaded using a rubber spatula with a shearing action. The resulting cookie dough was trimmed to the shape of a disk about 3 cm in diameter and baked in an oven at 180° C. for 10 minutes to provide 40 Smilax china Linne-containing cookies.

Formulation Example 2
(Vanishing Cream)

In a 200 ml beaker, the hot water extract of Smilax china Linne as prepared in Production Example 1 was concentrated by heating to 100 ml. This concentrate was mixed with 12.0 g of propylene glycol, 1.5 g of sodium lauryl sulfate, 0.025 g of methyl p-hydroxybenzoate and 0.015 g of propyl p-hydroxybenzoate under vigorous stirring to give a solution at 75° C. Meanwhile, 25.0 g of white petrolatum and 25.0 g of stearyl alcohol were melted in a 200 ml beaker on a hot water bath at 75° C. with vigorous stirring. To this melt was added the solution prepared above. The mixture was allowed to cool gradually at room temperature under sufficient stirring to provide 165 g of a vanishing cream.

Formulation Example 3
(Fine Granules)

The hot water extract of Smilax china Linne as obtained in Production Example 4, 2.4 kg, was diluted with 4.8 kg of purified water, then sprayed on 20 kg of powdered sugar using a flow coater in the routine manner. The resulting granules were dried and crushed to provide 21.4 kg of fine granules.

Test Example 1
(A Therapeutic Trial in Asthmatic Bronchitis)

A 7-year-old boy. Because of severe coughing, vomiting after breakfast persisted for 2 weeks. The patient took the hot water extract of Production Example 1 twice daily, morning and evening, in a volume of 50 ml per dose. The frequency of coughing decreased and emesis ceased to occur at week 2 after the commencement of medication. The cough disappeared at week 6 and the medication was discontinued at week 8. During one year after discontinuation, no recurrence of cough has been encountered.

Test Example 2
(A Therapeutic Trial in Bronchial Asthma)

A 69-year-old man. At month 4 after the first episode of asthma, the patient took a bronchodilator (Theodur™, Nikken Kagaku K.K.) for 11 months, an antiasthmatic (Onon™, Ono Pharmaceutical Co., Ltd.) for 9 months, and at month 10 after the first attack, an antiallergic drug (Intal™, Fujisawa Pharmaceutical Co., Ltd.) for 4 months but no improvement in asthma ensued. At month 14, the use of bronchodilator and antiasthmatic was discontinued and the hot water extract of Smilax china Linne prepared in Production Example 1 was taken 3 times daily, in a volume of 20 ml per dose. The asthma ceased to appear at week 2 of this medication and the use of the extract was discontinued at week 4. At month 3 after this discontinuation, the administration of the antiallergic drug was also discontinued but there was no attack during the intervening period and no episode has been encountered at month 1 after discontinuation of the antiallergic, either.

Test Example 3
(A Therapeutic Trial in Bronchial Asthma)

A 38-year-old woman. The patient was diagnosed as having bronchial asthma 15 years ago and thence treated with a bronchodilator (Theodur™, Nikken Chemicals Co., Ltd.), a bronchodilator (Spiropent™, Teijin Limited) and an antiallergic drug (Celtect™, Kyowa Hakko Kogyo Co., Ltd.) without success, experiencing several asthmatic episodes a year during the past 14 years. Another antiasthmatic (Onon™, Ono Pharmaceutical Co., Ltd.) was additionally used for 2 months without success and was, therefore, discontinued. With the administration of the bronchodilator and antiallergic drug being continued, the hot water extract of Smilax china Linne prepared in Production Example 2 was used 3 times a day, 160 ml per dose, for 4 consecutive weeks. There was no asthmatic attack during this period and no episode has been encountered, either, at month 4 after discontinuation of the hot water extract of Smilax china Linne.

Test Example 4
(A therapeutic Trial in Atopic Dermatitis)

An 8-year-old boy. The extract of Production Example 3 was further concentrated on a mild fire to 2 ml and the concentrate was mixed with 140 g of a hydrophilic cream (Sahne Cream™, Eizai) to provide a hydrophilic cream. When this hydrophilic cream was applied to a lesion about 5 cm across on the right upper arm for 1 week, the eczema associated with atopic dermatitis healed and no recurrence was encountered during the subsequent 2-week period.

Test Example 5
(A Therapeutic Trial in Bronchial Asthma, Pollinosis and Atopic Dermatitis)

In 10 patients, the hot water extract of Smilax china Linne prepared in Production Example 1 was administered twice a day, morning and evening, in a volume of 30 ml per dose. In all the 10 cases, the severity of bronchial asthma was "moderate" according to The Japanese Society of Allergology severity criteria for bronchial asthma. Each patient's initials, sex and age, period of administration of the hot water extract of Smilax china Linne, diagnosis, symptomatic improvement rating, side effect, and serum IgE level are shown in Table 1. The degree of improvement in clinical condition was rated on a 5-grade scale of "markedly improved, improved, unchanged, slightly aggravated, and aggravated" and the patient's own impression was asked for and recorded.

As apparent from Table 1, the therapeutic agent for respiratory disease according to this invention not only ameliorated the clinical condition without any side effect but also depressed the serum IgE level as verified by blood biochemistry, with the persisting depression of serum IgE level even after suspension of administration, indicating its remarkable usefulness.

The 10 patients were on treatment with the following concomitant drugs.

Patient I. M. (male, aged 69):
   Theophylline (400 mg/day)
   Pranlukast hemihydrate (450 mg/day)
   Disodium cromoglycate (8 mg/day)

Patient H. M. (female, aged 38):
   Theophylline (400 mg/day)
   Oxatomide (60 mg/day)
   Pranlukast hemihydrate (450 mg/day)
   Clenbuterol HCl (20 μg/day)

Patient S. I. (female, aged 29):
   Theophylline (400 mg/day)
   Clenbuterol HCl (20 μg/day)
   Betamethasone (0.5 mg/day)
   α-Chlorpheniramine maleate (4 mg/day)
   Pranlukast hemihydrate (450 mg/day)

Patient T. Y. (female, aged 47):
   Theophylline (400 mg/day)
   Clenbuterol HCl (20 μg/day)
   Betamethasone (0.5 mg/day)
   α-Chlorpheniramine maleate (4 mg/day)
   Pranlukast hemihydrate (450 mg/day)

Patient H. K. (male, aged 9):
   Theophylline (320 mg/day)
   Oxatomide (20 mg/day)

Patient H. H. (male, aged 8):
   Theophylline (240 mg/day)
   Oxatomide (20 mg/day)

Patient Y. H. (female, aged 6):
   Oxatomide (20 mg/day)

Patient Y. H. (male, aged 11):
   Theophylline (480 mg/day)
   Oxatomide (30 mg/day)

Patient A. A. (male, aged 5):
   Theophylline (160 mg/day)
   Oxatomide (20 mg/day)
   Beclomethasone propionate (150 μg/day)

Patient Y. T. (male, aged 11):
   No concomitant drug

TABLE 1

| Patient | Sex | Age | Administration period | Diagnosis | Improvement in clinical condition | Side effect | Serum IgE level (IU/ml) | | | |
|---|---|---|---|---|---|---|---|---|---|---|
| | | | | | | | Before administration | After 1 month | After 2 months | After 3 Months | After 6 months |
| I. M. | M | 69 | 1 mon. | Bronchial asthma | Markedly improved | None | 103 | 89 | | | 38 |
| H. M. | F | 38 | 1 mon. | Bronchial asthma<br>Pollinosis | Markedly improved<br>Markedly improved | None | 394 | | 281 | | 261 |
| S. I. | F | 29 | 1 mon. | Bronchial asthma | Markedly improved | None | 256 | | 218 | | 149 |
| T. Y. | F | 47 | 1 mon. | Bronchial asthma | Markedly improved | None | 1,291 | | | 804 | 646 |
| H. K. | M | 9 | 2 mon. | Bronchial asthma | Markedly improved | None | 4,940 | | 3,020 | | |
| H. H. | M | 8 | 2 mon. | Bronchial asthma | Markedly improved | None | 1,443 | | 1,049 | | |
| Y. H. | F | 6 | 2 mon. | Bronchial asthma<br>Atopic dermatitis | Markedly improved<br>Markedly improved | None | 3,430 | | 1,272 | | |
| Y. H. | M | 11 | 1 mon. | Bronchial asthma<br>Atopic dermatitis | Markedly improved<br>Markedly improved | None | 5,770 | 5,280 | 3,920 | | |
| A. A. | M | 5 | 1 mon. | Bronchial asthma<br>Atopic dermatitis | Markedly improved<br>Markedly improved | None | 3,700 | 2,428 | | | |
| Y. T. | M | 11 | 3 mon. | Bronchial asthma<br>Atopic dermatitis | Markedly improved<br>Markedly improved | None | 1,388 | | 1,189 | 1,000 | |

The results in Table 1 indicate that Smilax china Linne, the active ingredient of this invention, is of use as a prophylactic or therapeutic agent for respiratory disease, such as bronchial asthma, and allergic disease, such as atopic dermatitis and pollinosis.

Furthermore, it has been confirmed that, as shown in Table 1, the administration of a hot water extract of Smilax china Linne resulted not only in a reduction in serum IgE level during the administration period but also in continued reduction even after suspension of administration and, thus, was effective in inhibiting the recurrence of respiratory disease and allergic disease even after suspension of administration.

Test Example 6
(A Therapeutic Trial in Psoriasis Valgaris)

A 38-year-old woman. The patient presented with characteristic silver-white scales in the elbow and the knee and severe injuries caused by the scratching because of severe pruritus. When the patient took 1.8 g of the fine granules prepared in Formulation Example 3 twice daily, morning and evening, remission of the scales and itchy sensation were obtained in a few days. In one week following initiation of medication, the detachment and diminution of the large lengthwise-extending lesion in the knee began to occur and by the end of a one-month-long continued medication, the detachment and diminution of the lesion had progressed still further and pruritus had also been relieved without any side effect.

Test Example 7
(A Therapeutic Trial in Pustular Psoriasis)

A 9-year-old boy. The patient persistently presented with severe desquamation and pruritus on the palms and soles. When the patient took 1.8 g of the fine granules prepared in Formulation Example 3 twice daily, morning and evening, the desquamation and pruritus began to subside at week 2. Then, further gradual remission ensued as the medication was continued, so that at 2 months no side effect was found and the symptom remained to have been palliated.

Test Example 8
(A Therapeutic Trial in Erythroderma Psoriaticum)

A 75-year-old man. Diffuse redness and silver-white scales were noted on the entire body but when the patient took 1.8 g of the fine granules prepared in Formulation Example 3 three times daily after meals, the scales disappeared and the redness also subsided at week 2. Further medication resulted in gradual remission of the lesions and at the end of 1 month of medication, the symptoms remained to have been palliated without signs of side effect.

Test Example 9
(A Therapeutic Trial in Palmoplantar Keratosis)

A 47-year-old woman. The patient presented with white to grayish white abnormal keratinization on both palms. When the patient took 1.8 g of the fine granules prepared in Formulation Example 3 three times daily after meals, the abnormal keratinization was normalized without side effect in one month of medication.

Test Example 10
(A Therapeutic Trial in Atopic Dermatitis)

An 11-year-old girl. On the first examination, dry skin and eczema were noted all over the face. Whereas the case had not responded to the earlier therapy including the administration of topical steroids at all, the intake of 1.8 g of the fine granules prepared in Formulation Example 3 twice a day, morning and evening, resulted in disappearance of the symptoms in one month and a half. No side effect was found at all.

Test Example 11
(A Therapeutic Trial in Carcinomatous Pain)

A 61-year-old man. To control the pain associated with cancer of the stomach, the patient was given 30 ml of the hot water extract of Smilax china Linne prepared in Production Example 1 twice daily. As a result, the pain disappeared completely in 2 days. No relapse of pain was complained of even after 6 months.

The above result indicates that Smilax china Linne is a useful prophylactic or therapeutic agent for the carcinomatous pain associated with various tumors and cancers such as stomach cancer as well.

Therefore, this invention is further concerned with a prophylactic or therapeutic drug for carcinomatous pain which comprises Smilax china Linne or a plant analogous thereto as the active ingredient and which is effective even in inhibiting the recurrence after suspension of medication.

What is claimed is:

1. A method of preventing or treating a respiratory disease, wherein the respiratory disease is bronchial asthma or asthamatic bronchitis, which comprises administering a therapeutically effective amount Smilax china, or an extract thereof, to a patient in need thereof.

2. A method of preventing or treating an allergic disease selected from the group consisting of atopic dermatitis, pollinosis, allergic rhinitis, and allergic conjunctivitis, said method comprising:

administering a therapeutically effective amount of Smilax china, or an extract thereof, to a patient in need thereof.

3. The method according to claim 2 wherein the allergic disease is atopic dermatitis or pollinosis.

4. The method according to claim 2 or 3 which comprises administering Smilax china root or stem or an extract thereof.

5. A method of preventing or treating carcinomatous pain which comprises administering an effective amount of a member of the genus Smilax, or an extract thereof, to a patient with carcinomatous pain.

6. The method according to claim 5 which comprises administering the root or stem of a member of the genus Smilax or an extract thereof.

7. The method as defined in claim 6 wherein said member of the genus Smilax is Smilax china Linneaus.

* * * * *

UNITED STATES PATENT AND TRADEMARK OFFICE
CERTIFICATE OF CORRECTION

PATENT NO.    : 6,309,674 B1
DATED         : October 30, 2001
INVENTOR(S)   : Masaya Tanaka and Masato Hiki It is certified that error appears in the above-identified patent and that said Letters Patent is hereby corrected as shown below:

<u>Title page,</u>
Item [73], Assignee,    Medion Research Laboratories,"
                            Hyogo (JP)
to
-- [73], Assignee,      Medion Research Laboratories, Inc. --
                            Hyogo (JP)

Signed and Sealed this

Twenty-sixth Day of March, 2002

Attest:

*Attesting Officer*

JAMES E. ROGAN
*Director of the United States Patent and Trademark Office*